(12) United States Patent
Smiley

(10) Patent No.: US 7,223,718 B2
(45) Date of Patent: *May 29, 2007

(54) ENHANCED GLYPHOSATE HERBICIDAL CONCENTRATES

(75) Inventor: Robert A. Smiley, Wilmington, DE (US)

(73) Assignee: Falcon Lab LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/074,046

(22) Filed: Mar. 7, 2005

(65) Prior Publication Data

US 2006/0199737 A1 Sep. 7, 2006

(51) Int. Cl.
*A01N 25/22* (2006.01)
*A01N 57/02* (2006.01)
*A01P 13/00* (2006.01)

(52) U.S. Cl. ..................................... 504/206; 504/362

(58) Field of Classification Search ................ 504/206, 504/362
See application file for complete search history.

(56) References Cited

U.S. PATENT DOCUMENTS

| | | |
|---|---|---|
| 3,799,758 A | 3/1974 | Franz |
| 3,853,530 A | 12/1974 | Franz |
| 3,977,860 A | 8/1976 | Franz |
| 4,140,513 A | 2/1979 | Prill |
| 4,315,765 A | 2/1982 | Large |
| 4,405,531 A | 9/1983 | Franz |
| 4,481,026 A | 11/1984 | Prisbylla |
| 4,507,250 A | 3/1985 | Bakel |
| 4,840,659 A | 6/1989 | Franz |
| 5,106,410 A | 4/1992 | Puritch et al. |
| 5,196,044 A | 3/1993 | Caulder et al. |
| 5,543,562 A | 8/1996 | Moreno et al. |
| 5,700,759 A | 12/1997 | Caulder et al. |
| 5,919,733 A | 7/1999 | Sedun et al. |
| 5,994,269 A | 11/1999 | Bugg et al. |
| 5,998,332 A | 12/1999 | Sato et al. |
| 6,034,034 A | 3/2000 | Caulder et al. |
| 6,323,156 B1 | 11/2001 | Smiley |
| 6,468,944 B1 | 10/2002 | Bugg et al. |
| 6,503,869 B1 | 1/2003 | Beste et al. |

OTHER PUBLICATIONS

Turner, D. J. "Effects on glyphosate performance of formulation, additives and mixing with other herbicides", Chapter 15 in The Herbicide Glyphosate, Grossbard et al, ed. Boston: Butterworths. p. 221-229. 1985.*

* cited by examiner

*Primary Examiner*—Sreeni Padmanabhan
*Assistant Examiner*—Renee Claytor
(74) *Attorney, Agent, or Firm*—Herbert M. Wolfson

(57) ABSTRACT

A herbicidal concentrate of a glyphosate di-salt and an enhancement agent is obtained by adjusting the pH of a concentrate containing a glyphosate salt until a single-phase concentrate is obtained. The amount of base added to the concentrate is generally the amount necessary to render a pH of about 7.0 to 8.5 to the concentrate.

17 Claims, No Drawings

ENHANCED GLYPHOSATE HERBICIDAL CONCENTRATES

FIELD OF THE INVENTION

A glyphosate herbicidal concentrate containing an enhancement agent is prepared by adding a base to the concentrate until the concentrate is single phase.

BACKGROUND OF THE INVENTION

One of the most popular post-emergent non-selective herbicides used around the world is glyphosate and salts of glyphosate including the monoammonium, diammonium and isopropyl ammonium salts disclosed in U.S. Pat. Nos. 5,998,332; 5,994,269; 5,196,044; 4,507,250; 4,481,026; 4,405,531; 4,315,765; 4,140,513; 3,977,860; 3,799,580; 3,799,758; and 3,853,530. Of these, the most widely sold non-selective herbicide in the world is the isopropylamine salt of N-(phosphonomethyl)glycine also named isopropylammonium glyphosate ("IPA glyphosate").

Like many post-emergent herbicides, glyphosates and salts of glyphosates are generally slow-acting, even with the addition of surfactants. Such slow responses of the targeted weeds to the herbicidal composition fail to provide the desired phytotoxicity of the formulation for days, sometimes even weeks. This is undesirable from the user's standpoint, especially for home and garden users where the herbicide is used for aesthetic purposes by the purchaser.

Over the years, developments have focused on alternative formulations capable of improving the rapidity of plant response to glyphosate salt formulations. U.S. Pat. Nos. 5,196,044 and 6,503,869, for instance, disclose enhanced herbicidal compositions wherein an enhancer, such as pelargonic acid or salts of pelargonic acid, is added to the glyphosate salt in order to decrease the time for plant response Such developments have resulted in the commercial availability of IPA glyphosate herbicidal formulations to home owners in so-called "ready-to-use" (RTU) forms that, when sprayed on the targeted weed, causes the weed to wilt, turn color and die in short time periods, sometimes as short as 24 hours or less. Such RTU formulations containing IPA glyphosate employ between from about 0.75 to about 2% by weight of IPA glyphosate with similar amounts of enhancing agents. The balance of the formulation is inactive ingredients, such as surfactants and water.

For economic reasons, it is advantageous to package and sell post-emergent herbicides in concentrated forms, i.e., formulations having low or no solvent content. Such concentrated formulations save both sellers and buyers the cost of storing and shipping water in which the herbicide ingredients are soluble. Furthermore such concentrates allow the end-user to vary his desired herbicidal treatment by diluting the concentrate with water to the strength needed, e.g., a high water dilution for easily killed weeds and a lower dilution for larger weeds or brush.

Previously, glyphosate concentrates containing as much as 53 weight percent glyphosate have been introduced to buyers-users in place of RTU formulations. However, such concentrates are still slow acting when diluted for use unless they are combined with a bipyridilium salt such as Diquat®, an EPA restricted material undesirable for use.

Some of the most effective enhancement agents, while compatible with IPA glyphosate at dilute concentrations, are not capable of being dissolved in concentrated IPA glyphosate solutions and therefore do not offer a practical solution to manufacturers for concentrated forms of glyphosate salts.

For example, commercially available unenhanced IPA glyphosate formulations typically contain from about 53.8 weight percent to as high as 62 weight percent IPA glyphosate in water. Attempts to incorporate enhancing agents, such as pelargonic acid or salts of pelargonic acid, into concentrated formulations have been unsuccessful in rendering homogeneous mixtures or solutions. This is attributable to chemical incompatibility. For example, when 18% or stronger IPA glyphosate in water is added to 40% or lower ammonium pelargonate in water, two liquid phases result, neither phase being soluble in the other. Such mixtures, having separate liquid phases, have no commercial value.

SUMMARY OF THE INVENTION

A herbicidal concentrate of at least one glyphosate di-salt and at least one enhancement agent may be prepared by adjusting the pH of a concentrate containing the glyphosate mono-salt and enhancement agent until a single-phase solution is obtained. Typically, the pH of the concentrate is adjusted to at least 7.0 by addition of a base.

The preferred enhancement agent is an ammonium salt of the formula:

$$R_1COO^-X^+ \quad (I)$$

wherein $R_1$ is a $C_7$ to $C_{11}$ hydrocarbyl group and X is ammonium ($NH_4^+$). In the formula (I), any of the hydrogen on $R_1$ may be substituted with one or more hydroxyl or $C_1$-$C_5$ hydrocarbyl group, such as an alkyl group. In a most preferred embodiment, the compound of formula (I) is ammonium pelargonate.

The preferred glyphosate mono-salt is the isopropylamine salt of N-(phosphonomethyl)glycine, or isopropylammonium glyphosate ("IPA glyphosate").

DETAILED DESCRIPTION OF THE PREFERRED EMBODIMENTS

The concentrate of the invention can be easily transported and thus offers great economic advantages. The concentrate contains at least one glyphosate di-salt and, as enhancement agent, at least one ammonium salt. Inclusion of the ammonium salt provides a means of enhancing the effectiveness of the post-emergent herbicide. Upon dilution, obtainment of a faster time for visualization of the herbicidal effect is noted. In addition, the presence of the ammonium salt permits lower amounts of the herbicidal active ingredient in the homogeneous concentrate. The reduction in the amount of the herbicidal active ingredient is desired for both economic and environmental reasons.

The compatibility of the concentrated glyphosate salt is the result of adjustment of the pH of the formulation. The resulting formulation, containing a di-salt of glyphosate, such as ammonium, isopropyl ammonium glyphosate, and enhancement agent, upon dilution, is fast acting and exhibits a broad spectrum of phytotoxic activity. The weight ratio of the glyphosate di-salt to enhancement agent in the herbicidal concentrate is generally between from about 1:1 to about 1:2.

The preferred enhancement agent is an ammonium salt of the formula:

$$R_1COO^-X^+ \quad (I)$$

wherein $R_1$ is a $C_7$ to $C_{11}$ hydrocarbyl group, preferably a saturated group, and X is ammonium ($NH_4^+$). In the formula (I), any of the hydrogen on $R_1$ may be substituted with one or more hydroxyl or $C_1$-$C_5$ hydrocarbyl group, such as an alkyl group. In a preferred embodiment, the enhancement agent is the ammonium salt of caprylic, pelargonic, capric, undecanoic or lauric acid. In a most preferred embodiment, the compound of formula (I) is ammonium pelargonate.

The glyphosate salt of the concentrate is preferably a di-salt of N-phosphonomethylglycines, especially the diammonium salts. Such salts are produced by the addition of a base to a solution containing the corresponding mono-ammonium salt and enhancement agent. In a preferred embodiment, the glyphosate salt of the concentrate is the di-salt ammonium(isopropylammonium)N-(phosphonomethyl)glycine or ammonium, (isopropylammonium)glyphosate.

The enhanced herbicide concentrates of the invention can be made by adding a base compound to the mono-glyphosate salt until a pH greater than 7.5 is obtained and then adding an ammonium pelargonate solution to the basic solution. A one phase concentrated herbicidal solution is therefore obtained. The preferred pH range of the concentrated solution is between from about 7.5 to about 8.5, more preferably as close to 7.5 as possible while still maintaining a single liquid phase.

Preferred base compounds are alkali and alkaline hydroxides, as well as ammonia and ammonium hydroxide. Further, base compounds include organic water-soluble amines, such as alkyl and dialkyamines like methylamine, dimethyamine, ethylamine, diethylamine, propylamine, isopropylamine and dipropylamine and aminoalcohols like ethanolamine, diethanolamine and similar substituted amines, as well as water-soluble polyamines.

The amount of the post-emergent glyphosate herbicide in the concentrated herbicidal composition is between from about 10 to about 50 weight percent, most preferably between from about 16 to about 32 weight percent. The amount of ammonium salt in the post-emergent herbicide may typically be between from about 16 to about 52 weight percent, preferably between from about 24 to about 32 weight percent. The concentrate can be diluted with water to render a RTU solution containing about 1 to about 2 weight percent glyphosate.

The invention can best be understood by reviewing the functionality of the three acid groups of N-(phosphonomethyl)glycine in relation to ammonium pelargonate, wherein one of the acid groups is internally neutralized by the amine group in glycine. The two remaining free acid groups are capable of reacting with bases to form salts. IPA glyphosate can be made by reacting N-(phosphonomethyl)-glycine with approximately one equivalent of isopropylamine. An unreacted acid group remains. As a result, IPA glyphosate in water exhibits a pH of less than 7.0 and is thus acidic. When ammonium pelargonate in water solution is added to IPA glyphosate in water (or vice versa), a water insoluble layer separates as a second liquid layer. When the pH of the two liquid phase mixture is adjusted upward to 7.5 or greater by the addition of a base capable of neutralizing the remaining free acid group, a one phase solution consisting of a solution of a pH neutral glyphosate salt and enhancing agent occurs. When such solutions are adjusted with water such that the weight percentage of glyphosate is between from about 0.75 to about 2%, the targeted weeds are killed at the same or a faster rate as a RTU formulation. The diluted concentrate further exhibits all of the other attendant desirable features of glyphosate post-emergent herbicides. It is believed that the diluted concentrate functions, not by a chemical reaction of the glyphosate with the targeted weed, but also by actually dissolving the cell walls of the leaves of the targeted weed allowing faster penetration of the active herbicide.

Adjustment of the pH of the concentrated solution to greater than 7.5, by the addition of a base, converts the mono-ammonium salt of glyphosate to a di-salt. For example, the addition of ammonium hydroxide to isopropylammonium glyphosate in water yields a mixed salt, namely ammonium, (isopropylammonium)glyphosate. Such salts can further be isolated as pure solid compounds by evaporation of the excess water. The result is ammonium, isopropylammonium glyphosate in solid crystalline form.

Many of the resulting salts are non-hygroscopic, i.e., they do not absorb water on exposure to moist air, and can be stored or transported as 100% herbicidally active ingredients for reconstitution in water for treatment for weed control.

Since the ammonium salt is capable of being isolated as a pure solid and is not hygroscopic, some of the solid non-hygroscopic mixed salts of glyphosate can be physically incorporated with the solid enhancement agent, such as ammonium pelargonate, to produce 100% active ingredient enhanced solid herbicides that can be stored and shipped as anhydrous herbicide. Such solid herbicides do not require additional surfactant since the pelargonate salt is a surface active agent itself, i.e. a soap.

The enhanced herbicidal concentrate of the invention can further be made by adding N-(phosphonomethyl)glycine to the ammonium salt in water. Sufficient water soluble base, e.g., two or more moles of base per mole of N-(phosphonomethyl)glycine, is then added to render a clear, single phase solution.

The concentrate may be diluted depending upon the needs of the end-user and will typically vary depending on the weeds to be controlled. A representative formulation, upon dilution, may contain between from about 0.10 to about 3.0% by weight of the herbicidal components.

The following examples illustrate the practice of the present invention in its preferred embodiments. Other embodiments within the scope of the claims herein will be apparent to one skilled in the art from consideration of the specification and practice of the invention as disclosed herein. It is intended that the specification, together with the examples, be considered exemplary only, with the scope and spirit of the invention being indicated by the claims which follow.

EXAMPLES

All percentages expressed herein, unless stated to the contrary, are in weight percent.

Example 1

To 368 parts of 62% isopropylammonium glyphosate (Cheminova Corp.) was added 61 parts of 28-30% ammonium hydroxide. The resulting clear solution was then added with stirring to 926 parts of 40% ammonium pelargonate solution. The resulting clear solution contained the equivalent, by weight, of 16.8% isopropylammonium glyphosate and 27.3% ammonium pelargonate. The pH of the concentrate was 7.5.

Example 2

The concentrated solution from Example 1 was diluted 1/15 with water producing a herbicidal treatment solution containing the equivalent of 1.05% IPA glyphosate and 1.7% ammonium pelargonate. This was designated as "E-R-1".

The following comparison was then conducted on the herbicidal properties of E-R-1 on 3-5 inch diameter wild pansy weed versus a 1.92% solution of IPA glyphosate prepared from Roundup Custom® (53.8% IPA glyphosate) and a 1.92% Roundup® prepared ready-to-use IPA glyphosate sold to homeowners in a spray bottle. The sprayer used in all cases was the same type sprayer used in commercially available Roundup® RTU formulations from Monsanto.

| Treatment | % Necrosis Hours after treatment | | | % Control Days after treatment | | |
| --- | --- | --- | --- | --- | --- | --- |
|  | 5 | 10 | 24 | 6 | 8 | 11 |
| Roundup Custom ® | 5 | 3 | 7 | 15 | 90 | 100 |
| E-R-1 | 22 | 50 | 69 | 71 | 97 | 100 |
| Roundup ® RTU | 2 | 2 | 76 | 65 | 95 | 100 |

E-R-1 prepared from the Example 1 concentrate was clearly the equivalent or superior to the performance of an RTU preparation or a herbicidal solution prepared from a commercial IPA glyphosate concentrate.

Example 3

A comparison of the same three treatments in Example 2 was made on the control of 8-12 inch diameter dandelion weed with the following results clearly showing the same or superior herbicidal efficacy of the concentrate prepared by the method of Example 1:

| Treatment | % Necrosis Hours after treatment | | | % Control Days after treatment | |
| --- | --- | --- | --- | --- | --- |
|  | 6 | 24 | 48 | 13 | 23 |
| Roundup Custom ® | 0 | 0 | 0 | 98 | 100 |
| E-R-1 | 45 | 61 | 84 | 100 | 100 |
| Roundup ® RTU | 20 | 48 | 60 | 98 | 100 |

Example 4

In a suitable beaker, 42.4 gm. of Monsanto "Aquamaster" herbicide concentrate containing 53.8% IPA glyphosate was added to 92.6 gm of 40% by weight ammonium pelargonate in water. Upon stirring, the mixture became more viscous and quickly separated into two liquid layers. The mixture was stirred again while 6.7 gm. of powdered 85% potassium hydroxide was slowly added. After the potassium hydroxide dissolved, a clear single phase liquid solution was obtained which contained 16% the equivalent of IPA glyphosate and 26% ammonium pelargonate, an enhanced glyphosate herbicide concentrate. The pH of the concentrate was approximately 8.0.

Example 5

In a suitable beaker, 37.4 gm. of 62% aqueous isopropylammonium glyphosate (Cheminova Corp.) was mixed with 99.75 gm. of 40% aqueous ammonium pelargonate solution. Two liquid phases were present which even after vigorous stirring would not dissolve in each other. Then, with stirring, 11.25 gm. of a 40% aqueous solution of dimethylamine was added. A clear, one liquid phase solution resulted which contained the equivalent of 15.4% isopropylammonium glyphosate and 26.9% ammonium pelargonate, an enhanced glyphosate herbicide concentrate.

Example 6

A mechanical mixture of 10 gm. of dry, solid isopropylammonium glyphosate and 20 gm. of dry, solid ammonium pelargonate was made by thoroughly grinding and mixing the two solids to assure a homogeneous powder. The resulting 30 gm. was exposed to the air in a weighing dish on a balance to determine if the mixture was hygroscopic or dry. There was no weight gain or loss after three days showing that the mixture was dry and not hygroscopic. To this mixture was further added 3 gm. of powdered 85% potassium hydroxide and the solids again thoroughly mixed. This solid mixture contained the equivalent of 30% isopropylammonium glyphosate and 60% ammonium pelargonate, being a solid enhanced glyphosate herbicide concentrate. When added to a liter of water to prepare a herbicide containing the equivalent of 1% IPA glyphosate and 2% ammonium pelargonate for enhanced weed treatment, a clear spray solution resulted.

Example 7

A 50 gm. portion of a 53.8% glyphosate solution as the isopropylammonium salt (Monsanto Aquamaster®) was placed in a glass shallow evaporating dish. To this was added 10 gm. of 28-30% ammonium hydroxide and the solution thoroughly mixed by slowly tilting the dish. The dish was then exposed to air at ambient conditions for 2 weeks during which time the water evaporated off leaving a white crystalline solid weighing 38.9 gm. This crystalline solid was non-hygroscopic as demonstrated by leaving it exposed to the air on a balance for three days. The weight stayed the same indicating that it was anhydrous and did not absorb water from the air. By the method it was prepared and the yield obtained it was determined to be the mixed salt ammonium, (isopropylammonium)glyphosate. The melting point was 200-205° C. (isopropyl ammonium glyphosate melts at 155-158° C.) The FT-IR spectrum in KBr is:

| Wave number (cm$^{-1}$) Position | Intensity |
| --- | --- |
| 1632.97 | 9.904 |
| 1106.84 | 14.970 |
| 1402.67 | 15.021 |
| 1166.18 | 15.317 |
| 3059.47 | 17.394 |
| 1041.52 | 19.947 |
| 1567.88 | 20.626 |
| 463.94 | 22.414 |
| 1430.89 | 22.931 |
| 2856.45 | 23.764 |
| 1313.04 | 24.469 |
| 1488.31 | 27.585 |
| 942.15 | 27.622 |
| 512.77 | 28.265 |
| 931.37 | 28.343 |
| 1203.02 | 30.685 |
| 993.84 | 31.160 |
| 786.42 | 33.097 |
| 875.65 | 36.530 |
| 574.01 | 42.708 |
| 1704.78 | 42.901 |
| 1272.49 | 44.548 |
| 443.47 | 47.398 |
| 1245.99 | 49.182 |

-continued

| Wave number (cm$^{-1}$) Position | Intensity |
|---|---|
| 2351.42 | 49.573 |
| 1338.75 | 49.818 |
| 597.17 | 51.904 |

Example 8

To 20 gm. of dry solid ammonium, (isopropylammonium) glyphosate was added 32.5 gm of dry solid ammonium pelargonate and the two solids thoroughly mixed by grinding together. To ensure that the mixture was compatible and non-hygroscopic, it placed on a weighing paper on a balance and exposed to the air for three days. There was no weight loss or weight gain, showing that the mixture did not pick up moisture from the air. The ratio of glyphosate as a salt to the ammonium pelargonate was 1:1.625. The mixture contained 38% glyphosate as the salt or 26% equivalent glyphosate acid. A 28 gm (approximately 1 oz. by weight) portion of the mixture was dissolved in a quart of water to give a slightly cloudy solution. This solution contained 1% glyphosate as a salt and 1.67% ammonium pelargonate. When it was sprayed on a patch of weedy turf, the sprayed area changed color and showed other visual signs of phytotoxicity within 2 hours and within 24 hours the entire sprayed patch bad turned brown and appeared dead.

From the foregoing, it will be observed that numerous variations and modifications may be effected without departing from the true spirit and scope of the novel concepts of the invention.

What is claimed is:

1. A single-phase herbicidal concentrate comprising an aqueous solution of a glyphosate di-salt and at least one ammonium compound represented by the formula $R_1COO^-X^+$ wherein $R_1$ is a $C_7$ to $C_{11}$ hydrocarbyl group, optionally substituted with one or more hydroxyl or $C_1$-$C_5$ hydrocarbyl groups and X is ammonium, wherein the following conditions exist:
    (a) the amount of glyphosate di-salt in the herbicidal concentrate is between about 10 to about 50 weight percent;
    (b) the amount of the at least one ammonium compound in the herbicidal concentrate is between from about 16 to about 52 weight percent; and
    (c) the pH of the herbicidal concentrate is from 7.0 to about 8.5.

2. The herbicidal concentrate of claim 1, wherein the weight ratio of glyphosate di-salt: ammonium compound in the concentrate is between from about 1:1 to about 1:2.

3. The herbicidal concentrate of claim 1, wherein the ammonium compound is an ammonium salt of caprylic, pelargonic, capric, undecanoic or lauric acid.

4. The herbicidal concentrate of claim 1, wherein the ammonium compound is ammonium pelargonate.

5. The herbicidal concentrate of claim 1, wherein $R_1$ of the ammonium compound is a saturated hydrocarbyl group.

6. The herbicidal concentrate of claim 1, wherein the glyphosate di-salt is a diammonium salt of glyphosate.

7. The herbicidal concentrate of claim 1, wherein the glyphosate di-salt is the isopropylamine di-salt of glyphosate.

8. A basic single phase herbicidal concentrate comprising 10-50% isopropylammonium glyphosate di-salt and 16-52% ammonium pelargonate, wherein the pH of the herbicidal concentrate is that sufficient to render a single-phase concentrate.

9. The herbicidal concentrate of claim 8, wherein the pH of the herbicidal composite is from about 7.0 to about 8.5.

10. The herbicidal concentrate of claim 8, wherein the weight ratio of the glyphosate salt ammonium compound in the concentrate is between from about 1:1 to about 1:2.

11. A method of preparing a single-phase herbicidal concentrate of a glyphosate salt which comprises introducing a sufficient amount of base to a concentrated mixture of a mono-salt of glyphosate and an ammonium compound of the formula $R_1COO^-X^+$ wherein $R_1$ is a $C_7$ to $C_{11}$ hydrocarbyl group, optionally substituted with one or more hydroxyl or $C_1$-$C_5$ hydrocarbyl groups and X is ammonium until a single-phase concentrate comprising a glyphosate di-salt is obtained.

12. The method of claim 11, wherein the amount of base added to the concentrated mixture is that sufficient to raise the pH of the concentrated mixture to between from about 7.0 to about 8.5.

13. The method of claim 11, wherein the ammonium compound is an ammonium salt of caprylic, capric, pelargonic, undecanoic, or lauric acid.

14. The method of claim 11, wherein the ammonium compound is ammonium pelargonate.

15. The method of claim 11, wherein the glyphosate di-salt is the diammonium salt of glyphosate.

16. The method of claim 11, wherein the glyphosate di-salt is the isopropyl amine di-salt of glyphosate.

17. The herbicidal concentrate of claim 1, wherein the glyphosate di-salt is the ammonium, isopropyl ammonium glyphosate di-salt.

* * * * *